United States Patent [19]

Rogers et al.

[11] Patent Number: 5,124,011
[45] Date of Patent: Jun. 23, 1992

[54] CYCLIC VOLTAMMETRY

[75] Inventors: Brian D. Rogers, Walden; Carl C. Smith, Burlington; Raymond L. Brisebois, Sudbury; John Ambrose, Oakville, all of Canada

[73] Assignee: Inco Limited, Toronto, Canada

[21] Appl. No.: 426,310

[22] Filed: Oct. 24, 1989

[51] Int. Cl.$^5$ .............................................. G25F 7/00
[52] U.S. Cl. ................................................. 204/153.1
[58] Field of Search .................................... 204/153.1

[56] References Cited

U.S. PATENT DOCUMENTS

| | | | |
|---|---|---|---|
| 3,925,168 | 12/1975 | Costas | 204/1 |
| 4,132,605 | 1/1979 | Tench et al. | 204/1 |
| 4,146,437 | 3/1979 | O'Keefe | 204/1 |
| 4,217,189 | 8/1980 | Kerby | 204/153.1 |
| 4,474,649 | 10/1984 | Goffman et al. | 204/1 |
| 4,624,857 | 11/1986 | Dahms | 427/8 |

OTHER PUBLICATIONS

Girgis et al., "Effect of Temperature on Cyclic Voltammograms During the Electrodeposition of Lead" Canadian Journal of Chemistry, vol. 67, No. 1, Jan. 1989, pp. 130–136.

Singh et al., "Screening Design Test For Cyclic Voltammetric Evaluation of Zinc Sulfate Electrolyte", J. Electrochem. Soc., vol. 132, Dec. 1985, pp. 2898-2903.

O'Keefe et al., "Electrochemical Evaluation of Zinc Sulfate Electrolyte Containing Cobalt, Antimony and Organic Additives", (1985), Proc. Int. Symp. on Phys. Chem. Extr. Metall., TMS, AIME, pp. 165-177.

O'Keefe, "Techniques For Evaluating Electrolytes For Metal Recovery", (1984), J. Electroanal, Chem., 168, pp. 131-146.

Wang et al., "The Influence of Additives and Their Interactions on Copper Electrorefining", Pro. Electrochem. Soc., (1984), pp. 655-670.

Krzewska et al., "Electrochemical Determination of Thiourea and Glue in the Industrial Cooper Electrolyte" Metallurgical Transactions, vol. 15B (Sep. 1984) pp. 451-459.

Bharucha et al., "Electrochemical Determination of Glue in Copper Refinery Electrolyte" Metallurgical Transactions B, vol. 9B, (Dec. 1978), pp. 509-514.

Vennesland et al., "Current-Potential Effects of Trace Impurities in Zinc Sulfate Electrolyte" Acta Chem. Scand., vol. 27, No. 3, (1973), pp. 846-850.

Conard et al., "Development of an Improved Method For Monitoring the Composition of Electrolyte in the Inco Copper Refinery Part 1: Executive Summary", Inco Ltd. (Jun. 15, 1987), pp. 1-11 (English) and pp. 1-12 (French).

Conard et al., "Development of an Improved Method For Monitoring the Composition of Electrolyte in the Inco Copper Refinery, Part 1: Executive Summary", Inco Ltd. (Nov. 15, 1986), pp. 1-15.

Primary Examiner—John Niebling
Assistant Examiner—Bruce F. Bell
Attorney, Agent, or Firm—Blake T. Biederman; Francis J. Mulligan, Jr.

[57] ABSTRACT

The invention provides a method of monitoring reagent levels in aqueous copper electrolytic solutions. To determine the amount of glue present in an electrowinning solution, potential is applied, decreasing in a cathodic direction (more negative) to initiate a first cycle peak. The first cycle peak is compared to a known to determine amount of glue in the solution. Additionally, voltage is cycled between upper and lower voltages to monitor glue/lignosulfonate ratios. Hysteresis and cycle stability are measured at reference voltages and compared to known hysteresis and cycle stability values to monitor glue/lignosulfonate ratio of electrolytic solutions.

20 Claims, 8 Drawing Sheets

COPPER SHEET PRODUCTION LESS POLARIZATION THAN LOWER TARGET LIMIT

COPPER SHEET PRODUCTION UPPER TARGET LIMIT

CYCLIC VOLTAMMETRY

This invention is related to control of copper electrochemical processing. More particularly, it is related to monitoring reagent levels in electrowinning of copper, electrorefining of copper and preparation of copper sheets for electrorefining copper.

BACKGROUND OF THE INVENTION

Three related processes are utilized in the electrolytic purification of copper. The processes include electrowinning, electrorefining and copper sheet production. Each process requires a unique combination of reagents to produce a high purity product at the highest possible efficiency. Electrowinning involves the direct electrodeposition of copper from an aqueous copper electrolyte to create a finished product. Electrorefining involves the purification of copper by dissolving an anode into solution and electrodepositing the dissolved copper as a high grade slab onto copper sheet or titanium mandrel. Copper sheet production involves a process of plating copper into thin sheets for use as starter sheets in a solution similar to electrorefining solutions. Copper sheet production is usually electrodeposited at a faster rate than that of electrorefining. Titanium mandrels may be stripped once a day, and to compensate for this electrolyte used for copper sheet production utilizes different reagent levels than that used for electrorefining.

Relatively small amounts of organic compounds such as glue, chloride, thiourea and Tembind TM (a lignosulfonate produced by Temfibre Inc. of Temiscaming, Quebec) are added to these electrochemical systems. Both excess supply and insufficient supply of these addition agents result in loss of current efficiency and copper deposit quality. Historically, it has been extremely difficult to control supply of these low level addition agents. The accepted practice has been to simply supply addition agents at constant rates which have been found to produce acceptable results through trial and error. However, in actual commercial electro-processing of copper the electrolyte composition and plating rates are often changing. For example, concentration of copper in the electrolyte and copper deposition rates frequently change. These changing conditions tend to adversely affect the quality of the copper deposited. Without any warning of the effect upon addition agent levels in the electrolyte, adjustments to the addition agents were not made until after production quality had suffered.

There are several possible electrochemical techniques for analyzing addition agent levels. The proposed techniques include potentiostatic transients, chronopotentiometry, cyclic galvanometry, differential pulse polarography, impedance measurements, stripping voltammetry and cyclic voltammetry. These electrochemical techniques have been successfully applied to lead, copper (using a thiourea addition agent) and zinc systems.

Cyclic voltammetry has been successfully used to measure additive levels of glue and antimony in zinc electrolyte (O'Keefe Canadian Patent 1,064,852). In the zinc electrolyte, glue and antimony levels were measured by measuring shifts in recorded portions of a cycle between cathodic deposition of zinc and anodic dissolution of the deposited zinc. However, in actual zinc electrolyte, both glue and antimony reagents are present. The zinc electrolyte process is controlled by trying to keep a pseudoequilibrium cyclic voltammogram plot at or near an ideal condition.

Additionally, in O'Keefe's Canadian Patent 1,064,852, control of a synthetic copper sulfate solution electrolyte having thiourea, chloride and glue reagents, was tested. The electrolyte was also tested in pseudo-equilibrium conditions and revealed that thiourea increased the polarization and caused a current peak at about $+0.190$ V. The method of O'Keefe does not teach testing of glue with Tembind rather than thiourea. To date, O'Keefe's cyclic voltammetry has not been successfully applied commercially in the copper electro-processing industry.

Recently, ASARCO (U.S. Pat. No. 4,474,649) has developed a differential pulse polargraphy technique for testing thiourea concentration in electrolyte used in copper electrorefining operations. This technique has become commercially acceptable for testing thiourea levels in the portion of the copper electrorefining industry using thiourea. However, to date, the differential pulse polarography method has not been adaptable to measure glue with Tembind.

Accordingly, it is an object of this invention to provide a process of effectively monitoring glue with Tembind in complex copper electrolytic solutions.

It is another object of the invention to provide a method of maintaining copper electrodeposition at levels of maximum quality and peak efficiency.

It is still another object of the invention to accurately measure glue concentrations on the order of a few parts per million in copper electrowinning solutions.

SUMMARY OF THE INVENTION

The invention provides a method of measuring amount of glue in an aqueous copper electrolytic solution. A potential is first applied through a sample of the aqueous copper electrolytic solution. The potential is decreased in a cathodic direction to electrolytically deposit copper from the sample onto a working electrode to initiate a first cycle peak of relatively rapid current increase. Location of the first cycle peak of the sample is measured as a function of potential. The location of the first cycle peak of the sample is compared to a location of a first cycle peak of a known glue level, measured under conditions similar to the sample, to determine the amount of glue in the electrolytic solution.

Additionally, the invention provides a method to monitor glue and Tembind in combination in an aqueous copper electrolytic solution. A potential is first applied through a sample of the aqueous copper electrolytic solution. The potential is cycled between a cathodic predetermined upper voltage to deposit copper on a working electrode and a more cathodic predetermined lower voltage at sufficient speed to prevent equilibrium conditions in the sample. Hysteresis of the current of the sample is measured at a predetermined hysteresis reference voltage. The hysteresis reference voltage has a voltage between the upper and lower voltages. The measured hysteresis of the current of the sample is then compared to a hysteresis target, measured under conditions similar to the sample to determine effectiveness of glue and Tembind in the electrolytic solution.

The invention also provides an alternative method of applying cyclic voltammetry to monitor glue and Tembind in combination in an aqueous copper electrolytic solution. A potential is applied through a sample of the aqueous copper electrolytic solution. The potential is cycled between a cathodic predetermined upper voltage to deposit copper on a working electrode and a more cathodic predetermined lower voltage at sufficient speed to prevent equilibrium conditions in the sample. At least a portion of the copper deposited on the working electrode remains deposited with each cycle. The cycling of the potential between the upper and lower voltages is repeated for a fixed number of additional cycles. Cycle stability (separation) is measured between at least two different cycles at a predetermined cyclic stability reference voltage. The reference cycle stability voltage has a voltage equal to or between the upper and lower voltages. The measured cycle stability of the sample is then compared to a cycle stability target measured under conditions similar to the sample to determine effectiveness of glue and Tembind in the electrolytic solution.

DETAILED DESCRIPTION OF THE INVENTION

The invention involves a method of conducting and analyzing cyclic voltammetry to determine the effectiveness of glue and Tembind in electrochemical deposition of copper. The invention measures reagent levels in electrowinning. In addition, for electrorefining and copper sheet production, the invention compares sample voltammograms to "target voltammograms" which were established during periods of good electrorefined cathode quality and copper sheet production. The same equipment and similar measurements are used to control reagents in all three copper electrodeposition processes.

Figure 1:
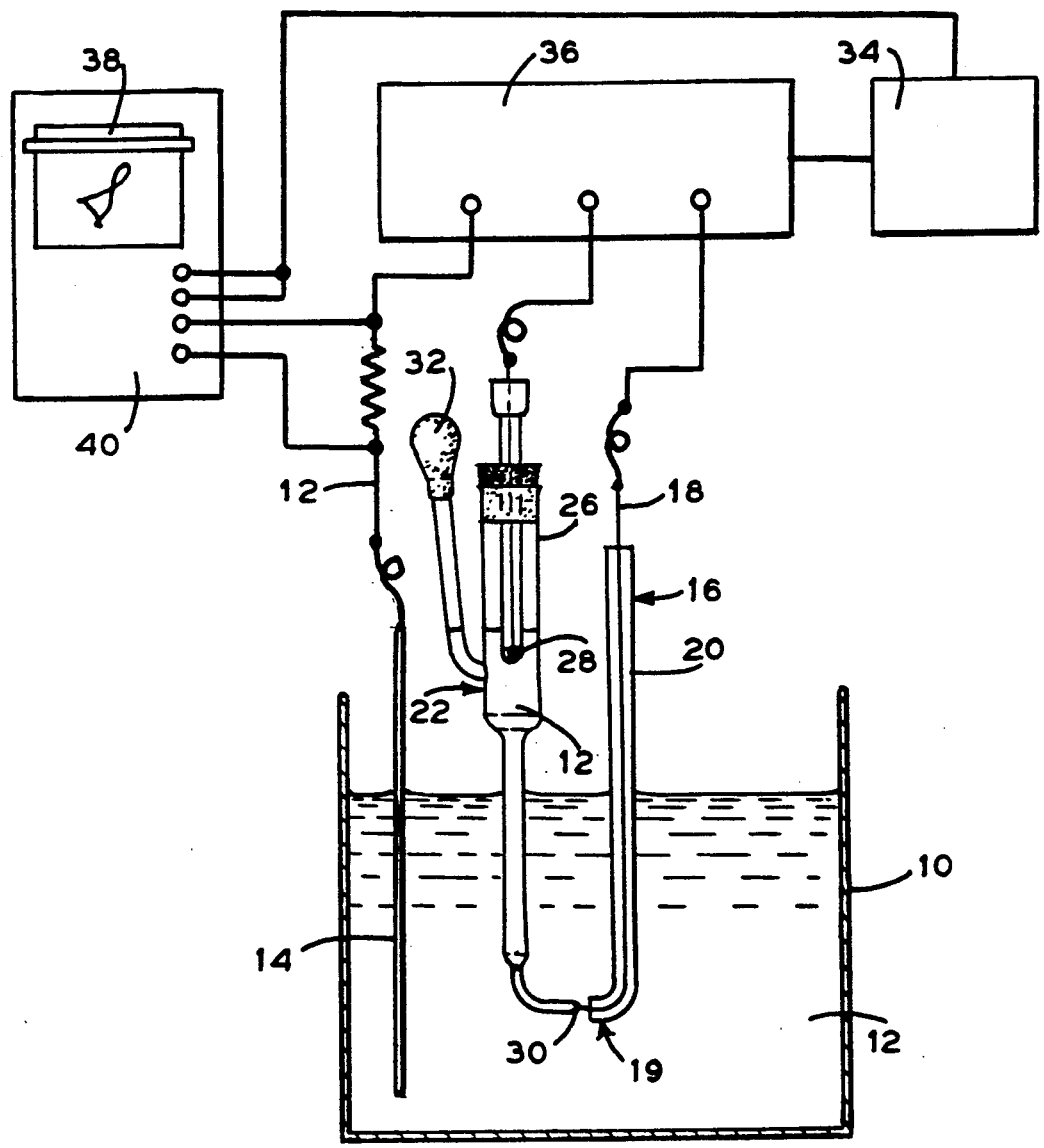
FIG. 1 is a schematic drawing of the electrolyte testing equipment.

In FIG. 1, the test cell 10 consisted of a 150 ml beaker containing an aqueous copper electrolyte 12. A strip of copper served as the counter electrode 14. A working electrode 16 consisted of a platinum wire 18 which operated best when mounted within a polyethylene coating 20. Coating 20 covered all of platinum wire 18 within electrolyte 12 except for the tip surface of the immersed end 19. Reference electrode compartment 22 was filled with an electrolyte 12 within a glass housing 26 and contained a mercury/mercurous sulfate reference electrode 28. Mercury/Mercurous sulfate reference electrode 28 contained $K_2SO_4$ solution 29 and a porous frit cover to allow electron transfer, but to prevent mixing of $K_2SO_4$ with electrolyte 12. Optionally, the reference electrode 28 could be constructed of an alternative material such as copper wire. A mercury/mercury sulfate reference electrode 28 was chosen because it does not introduce $Cl^-$ into electrolyte, as the more commonly used saturated calomel electrode would. NaCl or HCl is often added to electrorefining electrolytes for the recovery of silver. The reference electrode compartment 22 was positioned with its tip or Luggin capillary 30 positioned proximate to the platinum surface of immersed end 19 of working electrode 16 without Luggin capillary 30 directly contacting the surface of working electrode 16. This proximate positioning is important to accurately measure potential at the electrode surface with minimal contribution of internal resistance drop from the electrolyte 12. Rubber bulb 32 is used to control the level of electrolyte 12 within reference electrode compartment 22.

An ECO ™ model 567 function generator 34 and and ECO ™ model 550 potentiostat 36 were used to generate a potential across the electrolyte 12. A Hewlett-Packard ™ model 7090A X-Y plotter 38 connected to a microcomputer 40 was utilized to record voltage and current during each cycle. The microcomputer 40 may also be programmed to instruct plotter 38 to determine a plotter scale for specific test conditions, draw grids, label axes and may have the ability to store test data.

The following procedure was used to test each sample in a reliable and reproducible manner. Samples of electrolyte 12 were first cooled to 23° C. The samples were lab aged at least one hour, preferably between 1 and 4 hours and most preferably about 3 hours, to prepare the samples for testing. The potentiostat 36 and wave form generator 34 were first set to cycle from an upper voltage level of −400 mV to a lower of −600 mV at 10 mV/sec. For a copper reference electrode these values would be different, for example, (−25 mV to −225 mV). The scan rates of the voltammograms were selected to be sufficient to prevent the formation of equilibrium or pseudoequilibrium conditions which would adversely affect features of the voltammograms measured. Scan rates between 5 mV/sec and 10 mV/sec are preferred rates for producing the desired electrochemical effects in the sample. The voltage level range of −400 mV to −600 mV exists entirely within the region for cathodically depositing copper. As the potential cycles between −400 mV and −600 mV, copper is continuously electrodeposited on working electrode 16. The cycle should not be extended in the anodic direction to the point where copper completely dissolves from working electrode 16 which begins above about −400 mV versus the mercury/mercurous sulfate reference electrode. The cathodic limit of −600 mV versus the mercury/mercurous sulfate reference electrode was chosen because beyond this point the current sometimes goes through a maximum. This maximum is possibly due to deposition of Cu powder or even $H_2$ evolution.

Before testing samples of electrolyte 12, the counter electrode 14 was placed in 2% $H_2SO_4$ solution for 5 minutes and then rinsed with tap water followed by a distilled water rinse 3 times. The working electrode 16 was cleaned by dipping it into 1:1 $HNO_3$ until 15 seconds after all copper dissolved, washing it with distilled water, then placing it in 10% $H_2SO_4$ to cathodically clean it for 30 seconds at $-4$ V and washing it again with distilled water. Having the counter and working electrodes 14 and 16 clean is important for having reproducible results. With the cleaned counter electrode 14 and working electrode 16 prepared, the electrolyte beaker 10 was raised until the reference electrode compartment tip 30 was submerged approximately 2.5 cm. The potential was then cycled from $-400$ mV to $-600$ mV at $-10$ mV/sec and back to $-400$ mV at $+10$ mV/sec. This process was repeated five times. The quantity of cycles may be varied, depending upon what features are being measured. Preferably, current and voltage through each cycle are recorded directly with the plotter 38. To distinguish the five cycles, ideally each cycle of the plotter 38 is recorded in a different color.

Many months of research on both synthetic and actual electrolytes were required before the techniques of the invention were discovered. Testing of synthetic solutions indicated certain trends affecting voltammograms including amount of reagent, temperature of the electrolyte and age of the electrolyte. It was discovered that reagents of synthetic solutions and reagents of commercial electrolytes from tankhouse solutions had different effects upon voltammograms.

Figure 2:
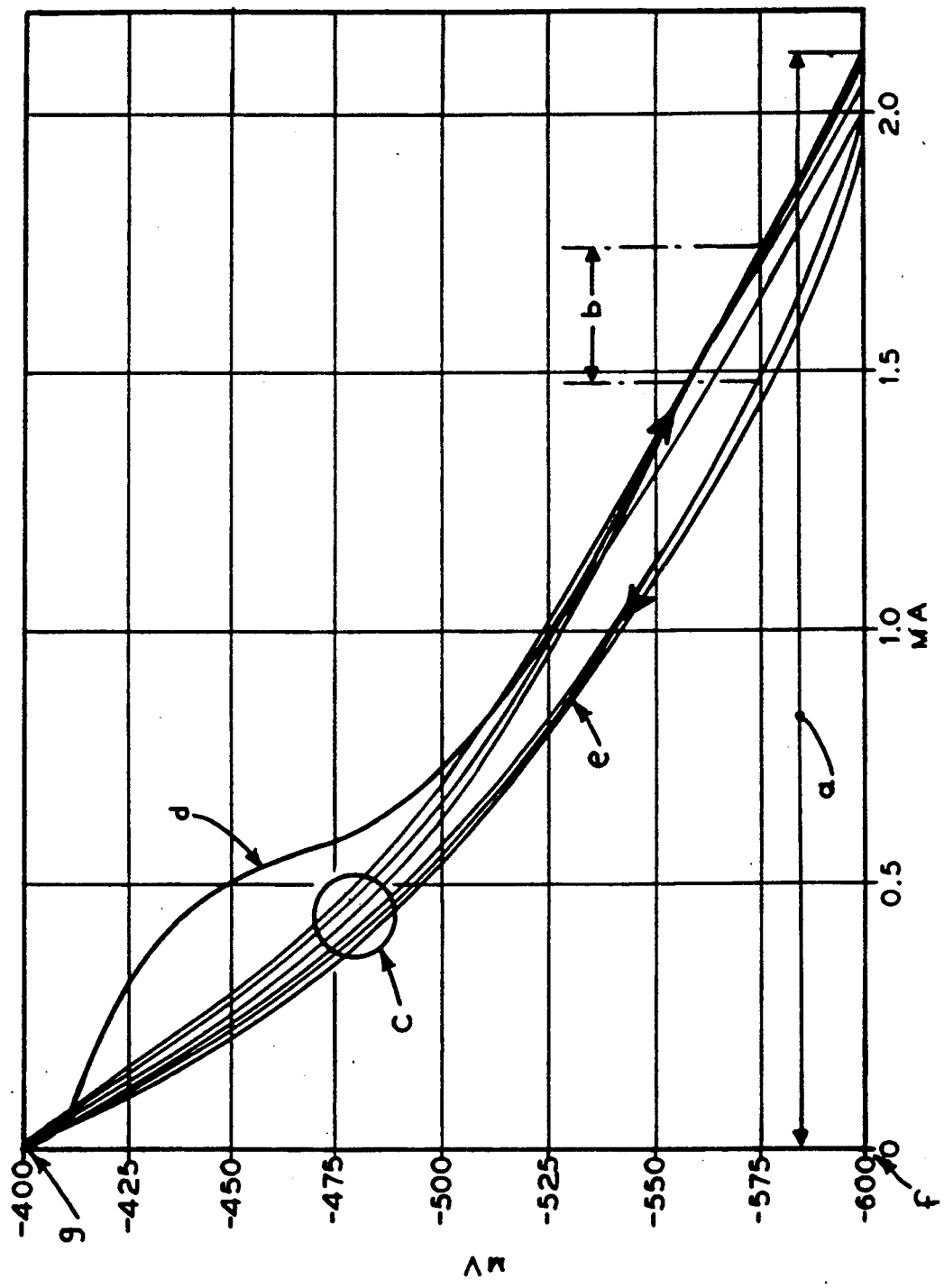
FIG. 2 is a schematic drawing of a voltammogram.

During testing it was discovered that certain features or characteristics could be harnessed to effectively monitor the copper electrolytes. Referring to FIG. 2, the factors which looked promising were polarization indicator (a), hysteresis (b), cycle stability (c), first cycle peak (d) and cycle crossover (e). Polarization indicator (a) is defined by the current flow in amperes in relation to potential. Polarization may refer to a current flow at a particular voltage or it may refer to the general current flow characteristics as a function of voltage over a range of voltages. At the particular voltage, polarization is said to have increased when the current decreases. Hysteresis (b) is defined as the change in current flow at a particular reference voltage between cycling in the cathodic direction and the anodic direction. To test hysteresis (b), it is necessary that only one cycle be made between lower voltage potential (f) and upper voltage potential (g). Cycle stability (c) is a measure of current shift at a reference voltage between two cycles of the voltage through the sample. To test cycle stability (c), it is necessary that the cycle between lower and upper voltages (f) and (g) be repeated. Polarization (a), hysteresis (b) and cycle stability (c) are all measures of current or amperes. These measurements of current may be made by simply measuring X-axis distances of a standardized plot which is directly proportional to current flowing to the working electrode (16 FIG. 1). This current will be dependent upon the surface area of the working electrode. For example, a distance of 7.5 mm on a plot may be equal to 0.1 mA. First cycle peak (d) is the measure of the location and shape of a first cycle peak as a function of voltage. Cycle crossover (e) is simply the parameter of whether there is an intersection of current as a function of voltage upon the cycle between the lower and upper voltages (f) and (g).

Several general trends were discovered in testing major components of copper electrolyte solutions. Copper concentration has a large effect upon cyclic voltammograms. Increased copper concentration has the effect of increasing the polarization indicator at $-600$ mV. In other terms, increasing the copper concentration decreases the polarization. Thus, the polarization indicator provides a semi-qualitative measure of copper concentration. Increases of nickel concentration has an effect of slightly decreasing the polarization indicator at $-600$ mV, slightly offsetting the stronger effect of copper. The concentration of recycled sulfuric acid has a very slight effect on voltammograms. Increased sulfuric acid concentration slightly decreases the polarization indicator at $-600$ mV. Temperature has a large effect upon voltammograms. An increase in electrolyte temperature produces a very large increase in the polarization indicator. Due to the effect of temperature on polarization, all further test electrolytes were tested at one temperature to limit error. Chloride does not have an appreciable effect upon the voltammogram in commercial electrolyte solutions. However, chloride does have some effect upon synthetic solutions.

The invention has been successfully applied to three separate but related copper electrolyte systems. The electrolyte systems will be further explained in the order of electrowinning, electrorefining and copper sheet production.

The electrowinning electrolyte is the simplest of the three electrolytic solutions. The major reagent added to improve copper deposition is animal glue. Animal glue is a protein derivative formed primarily from animal skins, hides, bones and tendons. Animal glue is added to the electrolyte to control the quality of deposit (eliminate nodules) and to control adhesion between titanium mandrels or blanks and the electrodeposited copper. Through the method of the invention it was discovered that ideally, glue levels should be maintained around 3 ppm glue and between about 1.5 and about 4.5 ppm glue. If glue levels leave this range the cathode quality and operating efficiently fall significantly. Prior to the invention glue levels exiting the electrolyte were about 10 ppm glue and there was a major problem with nodular deposition of copper. With the method of the invention, the electrolyte is regularly monitored and the glue is maintained at or near proper levels which has increased operating efficiency and cathode quality.

The following effects have been attributed to increases in glue concentration: decrease in first cycle hysteresis at $-475$ mV, decrease in third cycle hysteresis at $-575$ mV, decrease in cycle stability between first cycles and third cycles at $-600$ mV and a characteristic shift and shape of a current peak which occurs during the first cycle. Decreases in glue concentrations have the opposite effect to that of increases in glue concentration. These parameters have been found to be primarily independent of fluctuations in copper concentration. To control the amount of glue in the electrolyte, values are collected for the above parameters for the upper and lower limits amount of glue having maximum efficiency and high quality of copper deposition. The amount of glue added or rate of adding glue is then adjusted so that sample voltammograms, taken about once a day, are maintained at or near the target range. This, in turn, maintains the electrodeposition of copper at the desired level of efficiency and quality.

Figure 4:
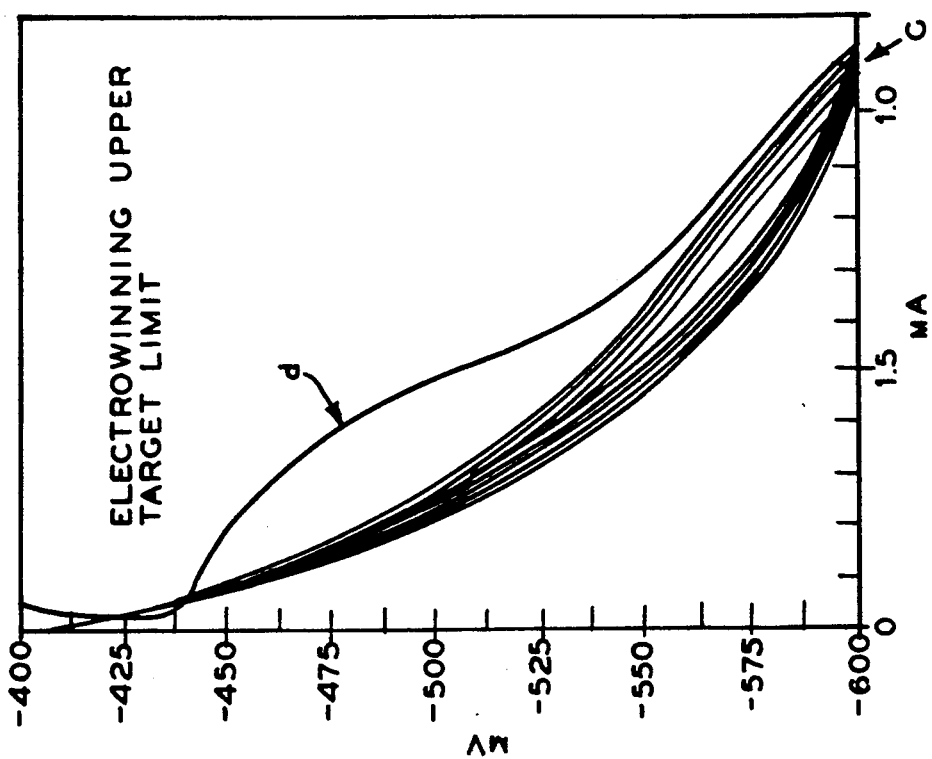
FIG. 4 is a voltammogram of an upper target limit of the solution of FIG. 3.
Figure 3:
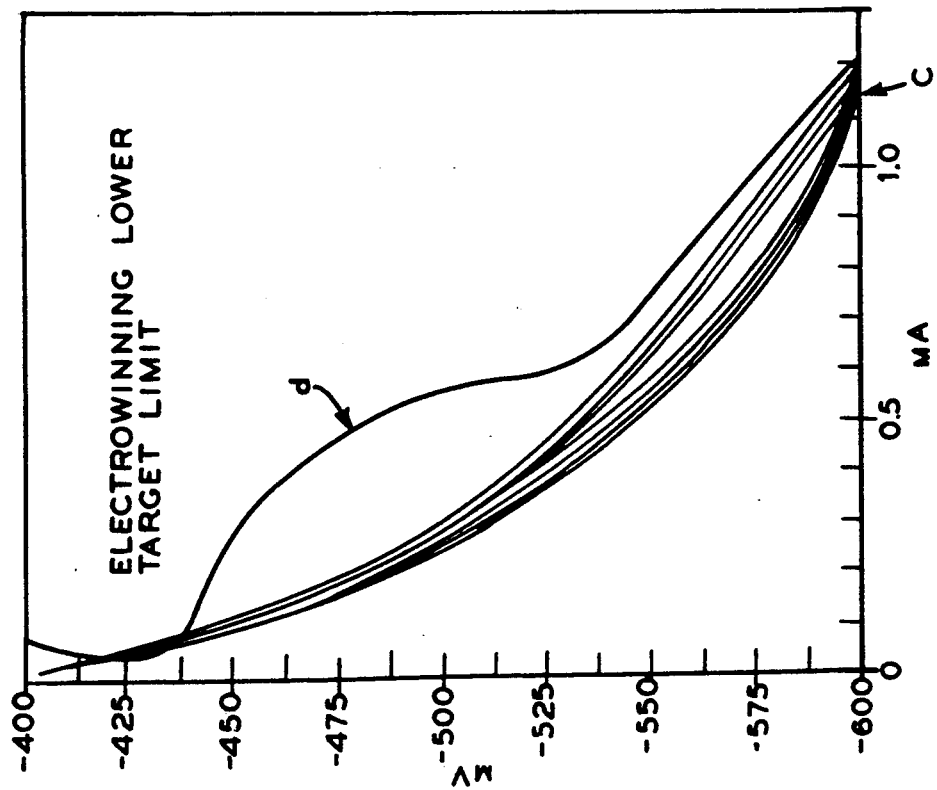
FIG. 3 is a voltammogram of a lower target limit for a copper electrowinning solution.
Figure 6:
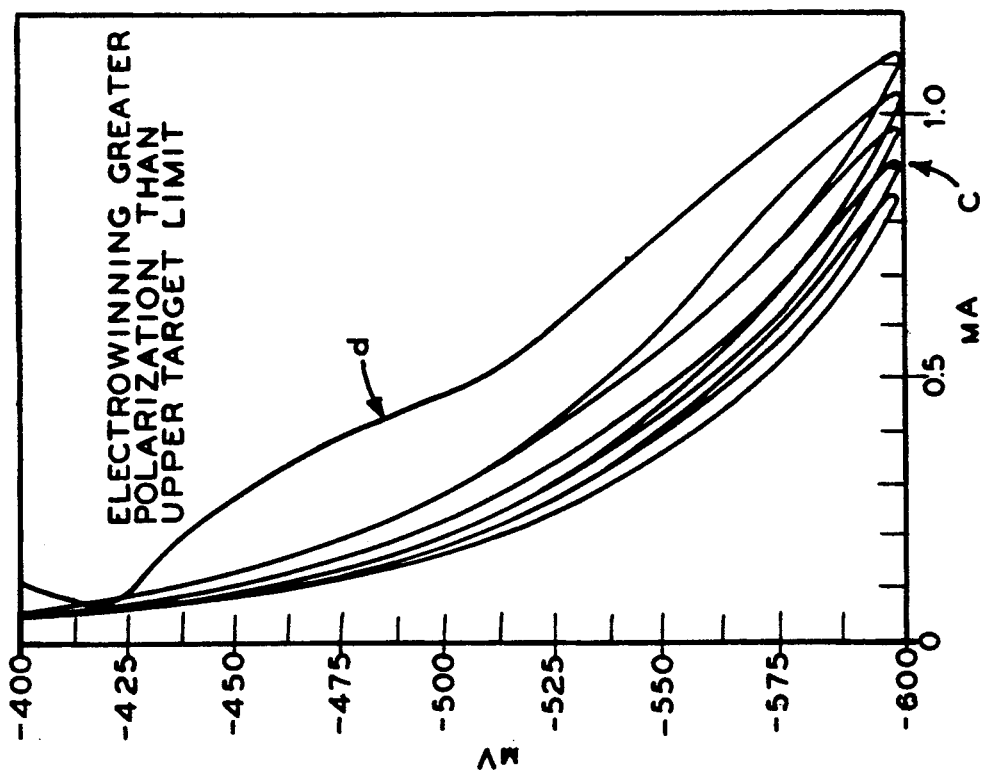
FIG. 6 is an example of a voltammogram of a copper electrowinning solution having greater polarization than the upper target limit of FIG. 4.
Figure 5:
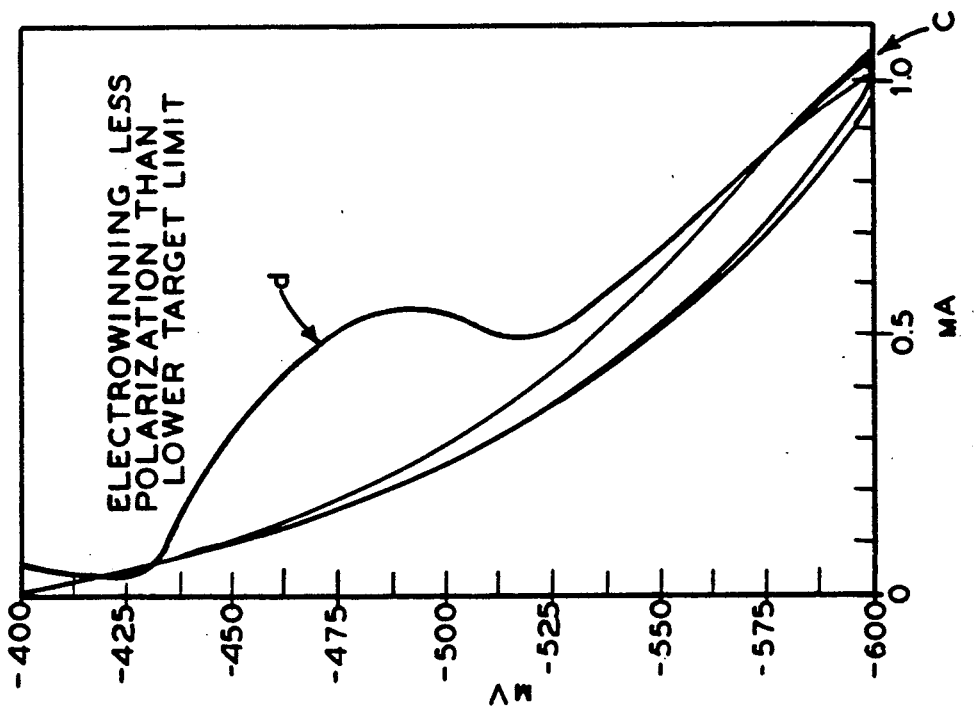
FIG. 5 is an example of a voltammogram of a copper electrowinning solution having less polarization than the lower target limit of FIG. 3.

In FIGS. 3 and 4, lower and upper target limits are defined by the total effect of all reagents. The electrowinning solution contains such reagents as glue, sulfuric acid and surfactant. The graph of FIG. 5 illustrates a solution with high cycle stability (c) at −600 mV, as cycles 2-5 are not as separated as FIG. 3. In addition, the first cycle peak (d), has shifted upward to indicate low glue levels. The electrolyte solution of FIG. 5 has insufficient polarization, in this situation the rate of addition of glue to the electrolyte would be increased. FIG. 6, shows a decreased cycle stability (c) at −600 mV and a first cycle peak (d) characteristic of excess glue levels. In the situation of FIG. 6, the rate of glue addition to the electrolyte would be decreased.

The method of the invention can accurately measure glue concentrations within 1.5 ppm in electrowinning solutions. This is done by comparing hysteresis and cycle stability value to hysteresis, cycle stability and first cycle peak to values for known glue concentrations. A semi-quantitative determination may be made by simply comparing voltammograms of samples to profile voltammograms having 0.0, 3.0, 6.0, 9.0, 12.0 and 15.0 ppm glue.

The electrorefining electrolyte is more complex and contains the reagents of glue, Tembind, chloride, sulfuric acid and copper. The following effects have been attributed to increased glue concentration: decrease in first cycle hyteresis at −475 mV, decrease in third cycle hysteresis at −575 mV, increase crossover during cycles 2 to 5 and a decrease of cycle stability between the first cycle and 3rd cycle at −600 mV. These effects are countered by the effect of Tembind, which has the following effects: increase in first cycle hysteresis at −475 mV, increase in third cycle hysteresis at −575 mV, decrease in crossovers during cycles 2 to 5 and increase in cycle stability between the first and third cycles at −600 mV. The two major effects which are monitored the closest for controlling electrorefining solutions are third cycle hysteresis at −575 mV and cycle stability at −600 mV. Voltammograms having a crossover during cycles 2 to 5 indicate very high polarization and excess glue in the electrolyte. To control glue and Tembind for the above solution, the above factors are recorded and compared to target voltammograms. Glue and Tembind are then adjusted accordingly to maintain the electrorefining solution at or near parameters of target voltammograms.

Figure 7:
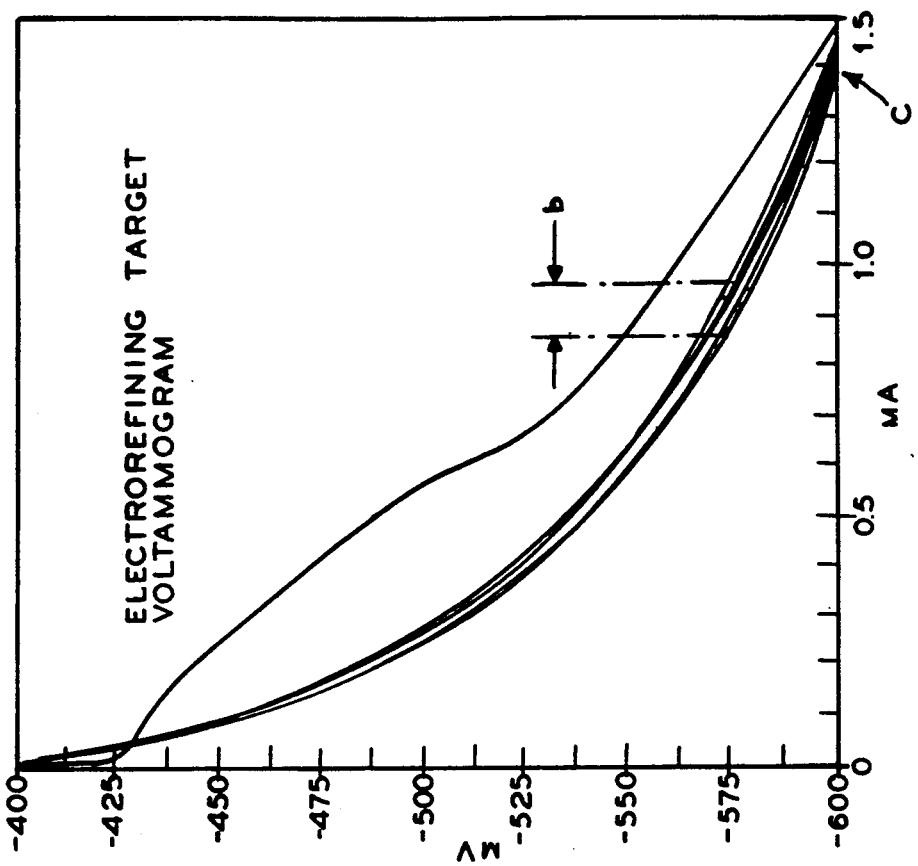
FIG. 7 is a target voltammogram of a copper electrorefining solution.
Figure 8:
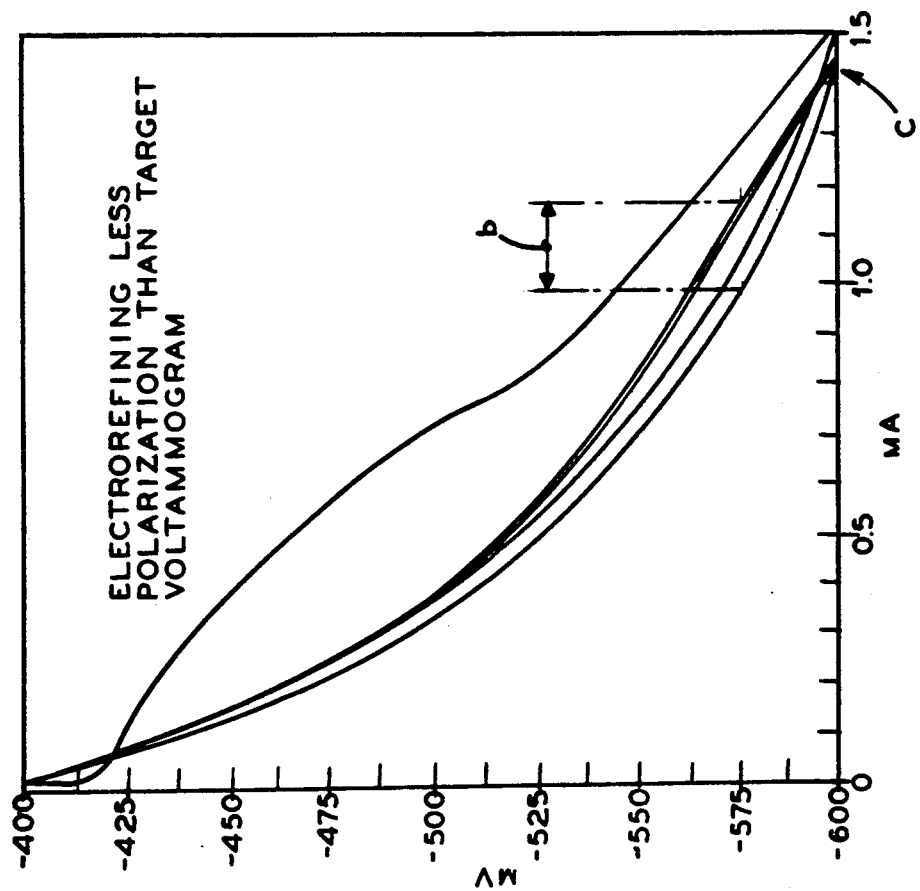
FIG. 8 is an example of a voltammogram of a copper electrorefining solution having less polarization than the target of FIG. 7.
Figure 9:
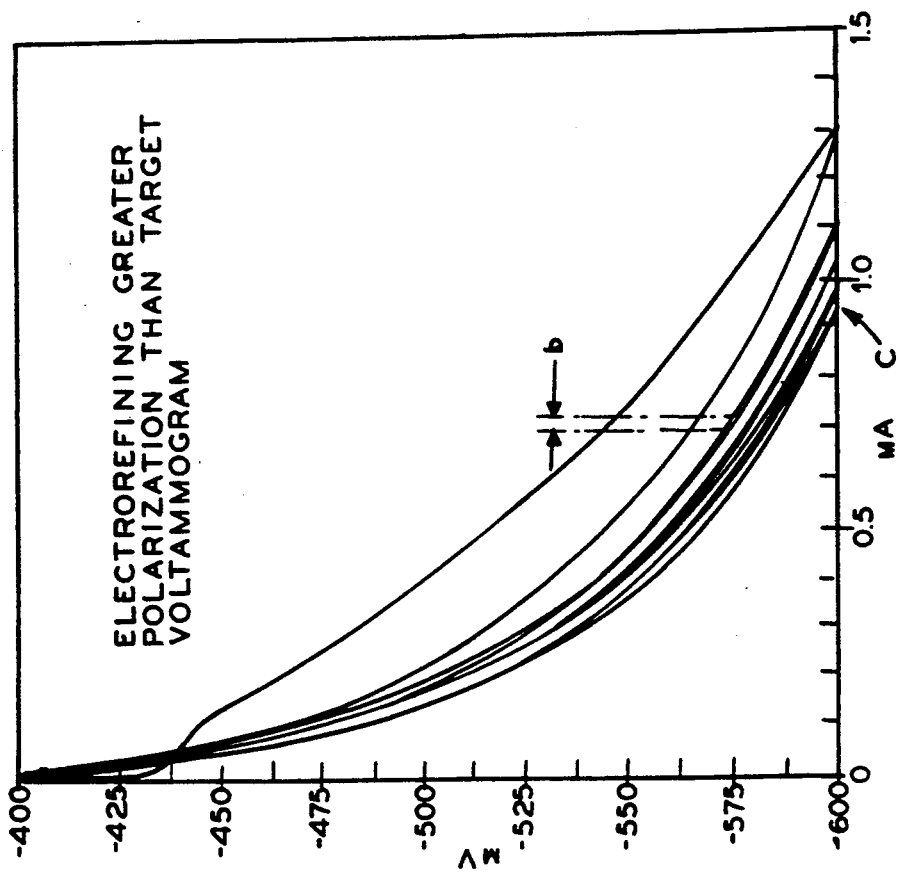
FIG. 9 is an example of a voltammogram of a copper electrorefining solution having greater polarization than the target of FIG. 7.

Referring to FIG. 7, a voltammogram for a target electrolyte solution, glue and Tembind are added at increased or decreased rates to adjust for any shift from the target voltammogram. FIG. 8 demonstrates a solution with increased cycle stability (c) at −600 mV and increased hysteresis (b) at −575 mV. The appropriate response to FIG. 8, a voltammogram of an electrolyte with insufficient polarization would be to either increase glue addition or decrease Tembind addition. FIG. 9 shows a solution with decreased cycle stability at −600 mV (c) and decreased hysteresis at −575 mV (b). Similarly, in response to FIG. 9, a voltammogram having excess polarization would be to either increase Tembind addition or decrease glue addition. Addition rate for reagents of glue and Tembind is critical for maintaining electrorefining operations at a high level of efficiency and producing high quality cathodic copper. Since the glue and Tembind in combination have opposite effects, the ratio of glue to Tembind if maintained, will effectively control the electrolyte. The ratio by weight of glue to Tembind added may, for example, be maintained around 0.48 for maintaining efficient electrorefining operations. The ratio of glue to Tembind added varies with the history of the solution. However, the target voltammograms appear to remain constant. The amounts of glue and Tembind change with changes in the operating systems such as a decrease in number of electrorefining cells. For this reason, addition ratios of glue and Tembind may be occasionally changed to compensate for changes in electrodeposition operations.

The method of the invention has been successfully applied to discover and correct problems in electrorefining tankhouse operations. Through cyclic voltammetry it was determined that glue and Tembind were not being distributed uniformly throughout two main electrolyte feedlines. Glue and Tembind were then added earlier in the main feed line to ensure mixing and uniform distribution of the glue. A glue injection pipe was also relocated to prevent a disproportionate amount of glue from exiting a bleed line. These adjustments in tankhouse setup have resulted in higher product quality (less nodular copper) at high operation efficiencies.

The electrolyte solution used for producing copper sheets (stripper electrolyte) contains the same reagents as the copper electrorefining solution. The starter sheets are electrodeposited at a higher current density than the electrorefining solution. An example, glue/Tembind addition ratio by weight of a stripper electrolyte would be about 1.6. Glue and Tembind have the same effects upon the stripper electrolyte as the electrorefining electrolyte. The same parameters are compared to parameters of target voltammograms to determine whether or not the addition of glue and Tembind should be altered.

Figure 10:
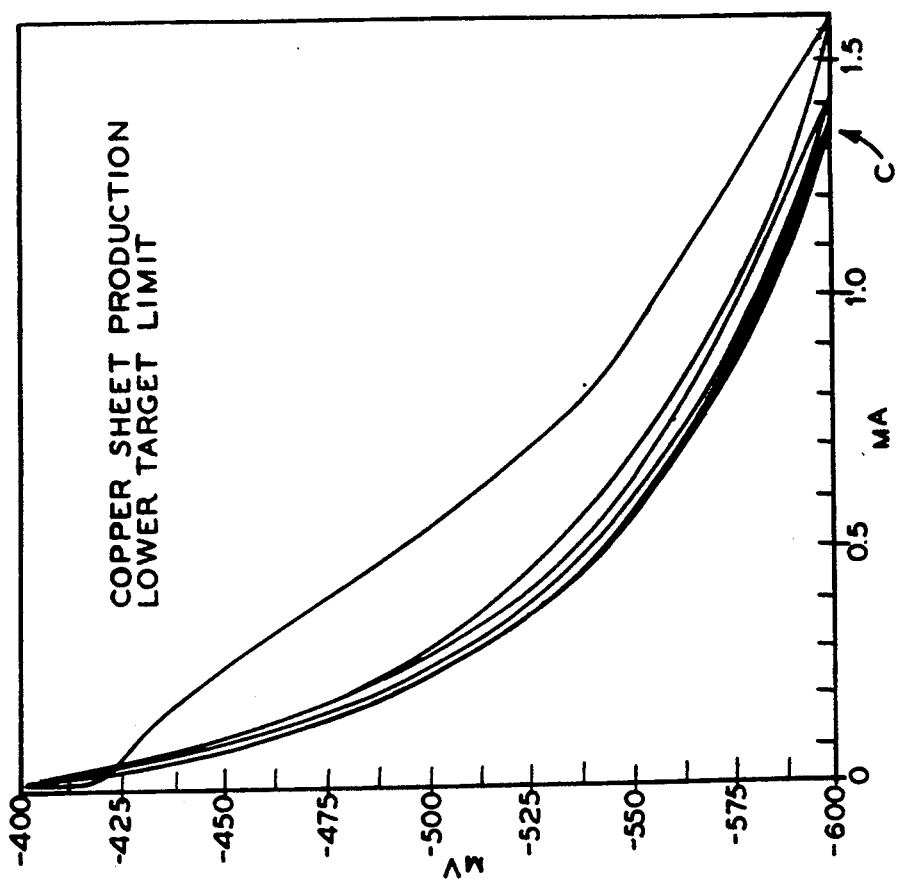
FIG. 10 is a voltammogram of a lower target limit of a copper electrolyte solution utilized for copper sheet production.
Figure 12:
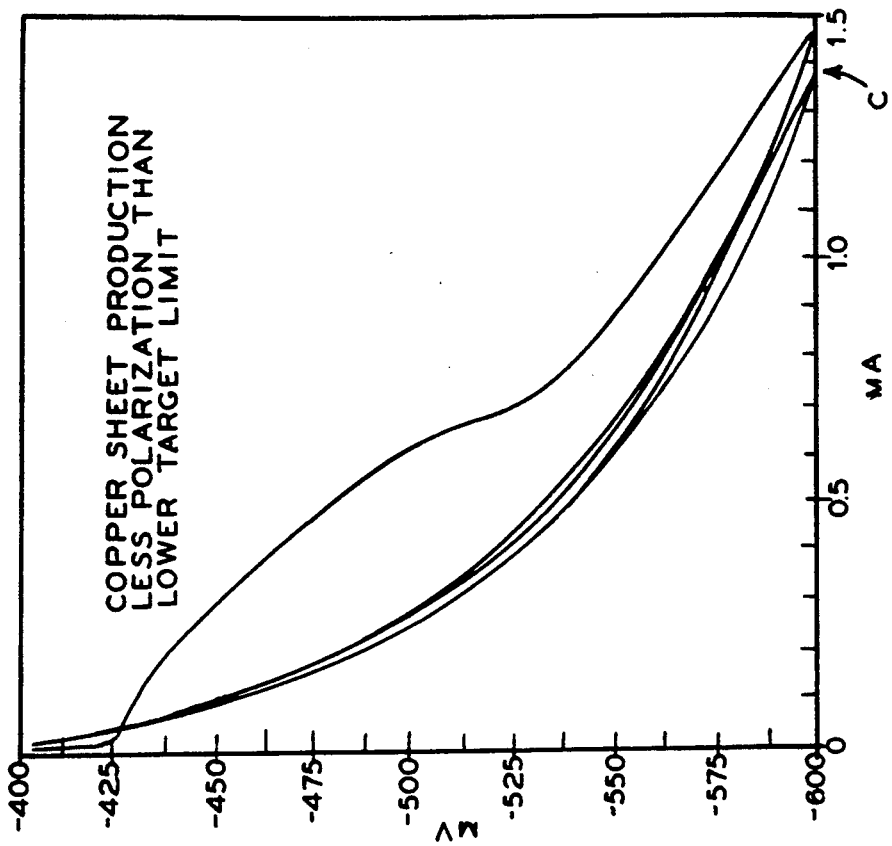
FIG. 12 is a voltammogram of an electrolyte utilized for copper sheet production having less polarization than the target of FIG. 10.
Figure 11:
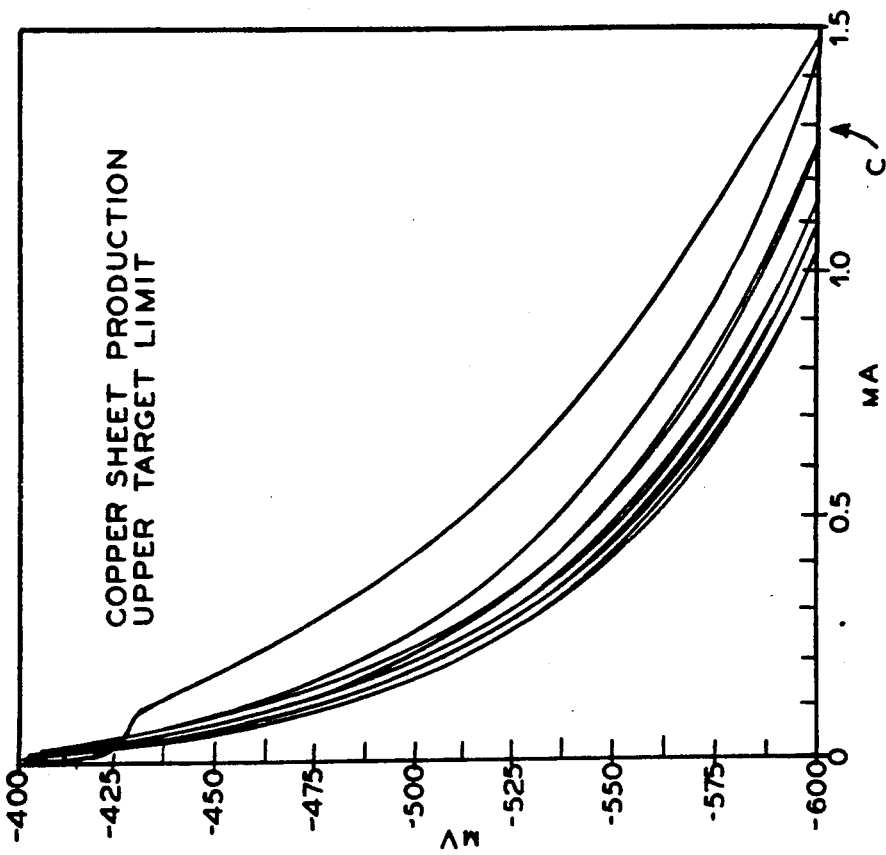
FIG. 11 is a voltammogram of an upper target limit of a copper electrolyte solution of FIG. 10.
Figure 13:
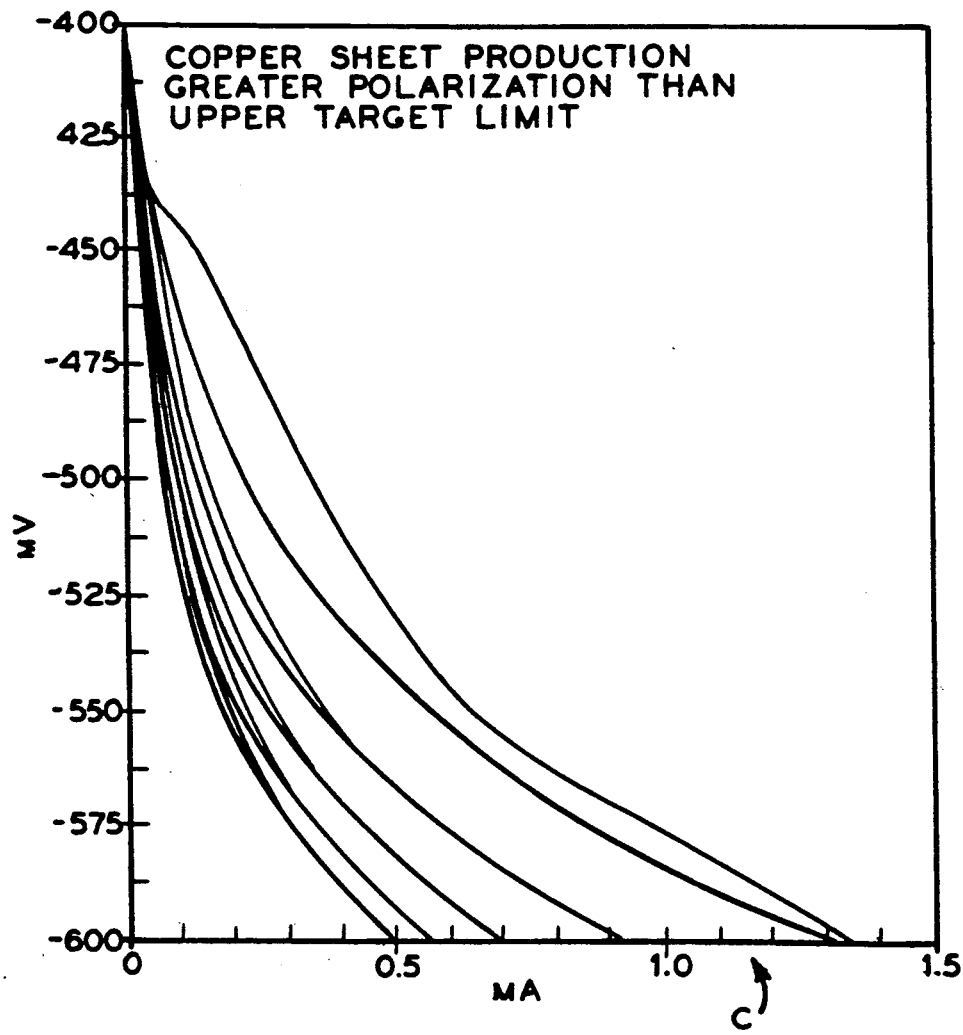
FIG. 13 is a voltammogram of an electrolyte utilized for copper sheet production having greater polarization than the target of FIG. 11.

The lower and upper target limits of FIG. 10 and 11 for the stripper electrolyte are quite different than the target for the electrorefining electrolyte of FIG. 7. The upper target limit of FIG. 11 contains crossover in the second to fifth cycles, indicating an increased amount of glue in relation to Tembind. FIG. 12 is an example of a sample electrolyte having cycles 2-5 at −600 mV bunched together (increased cycle stability c) and insufficient polarization. To correct the situation of FIG. 12, either less Tembind or more glue would have to be added to the electrolyte. FIG. 13, shows a solution having decreased cycle stability (c) at −600 mV. In addition, cycles 2-5 have crossovers which indicate decreased hysteresis. To return the electrolyte of FIG. 13 to within the target values, either more Tembind or less glue should be added. The major parameters compared are the third cycle hysteresis at −575 mV and the cycle stability between the first and third cycles. These parameters as in electrowinning and electrorefining are not significantly altered by changes in copper concentration.

Effective maintaining of the glue and Tembind in the stripper solution has a direct impact on starter sheet quality and stripability. If glue concentrations are too high, the deposit will be tough and have hard, dry stripping characteristics. If the glue concentration is too low, the deposit will be lacy having easy wet stripping characteristics. Periodic monitoring (once a day) with the method of the invention has proven to be an effective method of producing high quality sheets for electrorefining.

While in accordance with the provisions of the statute, there is illustrated and described herein specific embodiments of the invention. Those skilled in the art will understand that changes may be made in the form of the invention covered by the claims and that certain features of the invention may sometimes be used to advantage without a corresponding use of the other features.

The embodiments of the invention in which an exclusive property or privilege is claimed are defined as follows:

1. A method of applying cyclic voltammetry to measure amount of glue in an aqueous copper electrolytic solution comprising:
   applying a potential through a sample of said aqueous copper electrolytic solution,
   decreasing said potential in a cathodic direction to electrolytically deposit copper from said sample on a working electrode to initiate a first cycle peak of relatively rapid current increase,
   measuring location of said first cycle peak of said sample as a function of potential, and
   comparing said location of said first cycle peak of said sample to a location of a known glue level measured under conditions similar to said sample to determine the amount of glue in said electrolytic solution.

2. The method of claim 1 including the additional steps of:
   cycling said potential between a cathodic predetermined upper voltage to deposit copper on the working electrode and a more cathodic predetermined lower voltage at sufficient speed to prevent equilibrium conditions in said sample,
   measuring hysteresis of said current of said sample at a predetermined hysteresis reference voltage, said hysteresis reference voltage having a voltage between said upper and lower voltages, and
   comparing said measured hysteresis of said sample to a hysteresis target to determine the effectiveness of glue in said electrolytic solution.

3. The method of claim 1 including the additional steps of:
   cycling said potential between a cathodic predetermined upper voltage to deposit copper on a working electrode and a more cathodic predetermined lower voltage at sufficient speed to prevent equilibrium conditions in said sample, and having at least a portion of said copper deposited on said working electrode remaining deposited with each cycle,
   reapplying said cycling of said potential between said upper and lower voltages for a fixed number of additional cycles,
   measuring cycle stability of said sample between at least two different cycles at a predetermined cycle stability reference voltage, said cycle stability reference having a voltage equal to or between said upper and lower voltages,
   comparing said measured cycle stability of said sample to a cycle stability target measured under conditions similar to said sample to determine the glue level in said electrolytic solution.

4. The method of claim 3 including the additional steps of:
   measuring hysteresis of said current of said sample at a predetermined hysteresis reference voltage, said hysteresis reference voltage having a voltage between said upper and lower voltages; and
   comparing said measured hysteresis of said sample to a hysteresis target for a known glue level measured under conditions similar to said sample to determine the glue level in said electrolytic solution.

5. The method of claim 1 including the additional step of:
   recording current and voltage through said sample as said potential decreases in said cathodic direction.

6. The method of claim 1 including the additional steps of:
   aging said sample for at least one hour; and
   cooling said sample to about room temperature before said potential is applied to said sample.

7. The method of claim 1 wherein said potential is decreased in said cathodic direction at a rate between about 5 and about 10 millivolts per second.

8. A method of applying cyclic voltammetry to monitor glue and lignosulfonate in combination in an aqueous copper electrolytic solution comprising:
   applying a potential through a sample of said aqueous copper electrolytic solution,
   cycling said potential between a cathodic predetermined upper voltage to deposit copper on the working electrode and a more cathodic predetermined lower voltage at sufficient speed to prevent equilibrium conditions in said sample,
   measuring hysteresis of current of said sample at a predetermined hysteresis reference voltage, said hysteresis reference voltage having a voltage between said upper and lower voltages, and
   comparing said measured hysteresis of said sample to a hysteresis target to determine the effectiveness of glue and lignosulfonate in said electrolytic solution.

9. The method of claim 8 including the additional step of:
   recording current and voltage through said sample as the cyclic potential cycles between said upper and lower voltages.

10. The method of claim 8 including the additional steps of:
    aging said sample for at least one hour; and
    cooling said sample to about room temperature before said potential is applied to said sample.

11. The method of claim 8 wherein said upper and lower voltages cause cathodic deposition of copper on said working electrode.

12. The method of claim 8 wherein said lower voltage is about $-600$ mV and said upper voltage is about $-400$ mV.

13. The method of claim 8 wherein said cycling between said upper and lower voltages is performed at a rate between about 5 and about 10 millivolts per second.

14. A method of applying cyclic voltammetry to monitor glue and lignosulfonate in combination in an aqueous copper electrolytic solution comprising:
    applying a potential through a sample of said aqueous copper electrolytic solution,
    cycling said potential between a cathodic predetermined upper voltage to deposit copper on a working electrode and a more cathodic predetermined lower voltage at sufficient speed to prevent equilibrium conditions in said sample, and having at least a portion of said copper deposited on said working electrode remaining deposited with each cycle,
    repeating said cycling of said potential between said upper and lower voltages for a fixed number of additional cycles,
    measuring cycle stability of said sample between at least two different cycles at a predetermined cycle stability reference voltage, said cycle stability reference voltage being equal to or between said upper and lower voltages, comparing said measured cycle stability of said sample to a cycle stability target measured under conditions similar to said sample to determine the effectiveness of glue and lignosulfonate in said electrolytic solution.

15. The method of claim 14 including the additional steps of:
   measuring hysteresis of a current of said sample at a predetermined hysteresis reference voltage, said hysteresis reference voltage being between said upper and lower voltages; and
   comparing said measured hysteresis of said current of said sample to a hysteresis target measured under conditions similar to said sample to determine the effectiveness of glue and lignosulfonate in said electrolytic solution.

16. The method of claim 14 including the additional step of:
   recording current and voltage through said sample as said potential cycles between said upper and lower voltages.

17. The method of claim 14 including the additional steps of:
   aging said sample for at least one hour; and
   cooling said sample to about room temperature before said potential is applied to said sample.

18. The method of claim 14 wherein said upper and lower voltages cause cathodic deposition of copper on said working electrode.

19. The method of claim 14 wherein said lower voltage is $-600$ mV and said upper voltage is $-400$ mV.

20. The method of claim 14 wherein said cycling between said upper and lower voltages is performed at a rate between about 5 and 10 millivolts per second.

* * * * *